United States Patent [19]
Ellis et al.

[11] 3,964,477
[45] June 22, 1976

[54] METHOD OF USING ELECTRODES HAVING ANTISEPTIC PROPERTIES FOR LIDC THERAPY

[75] Inventors: Franklin H. Ellis; Stephen W. Andrews, both of Rochester, N.Y.

[73] Assignee: Sybron Corporation, Rochester, N.Y.

[22] Filed: Jan. 30, 1975

[21] Appl. No.: 545,609

[52] U.S. Cl. .............................. 128/172.1; 128/417
[51] Int. Cl.² ......................................... A61N 31/00
[58] Field of Search .............. 128/172.1, 417, 418, 128/416, 404, 410, 411, 419 R, 362, DIG. 4, 2.06 E, 2.1 E

[56] References Cited
UNITED STATES PATENTS

| | | | |
|---|---|---|---|
| 1,573,116 | 2/1926 | Kobayashi | 128/172.1 |
| 1,585,104 | 5/1926 | Montgomery | 128/172.1 |
| 2,121,875 | 6/1938 | Kruse et al | 128/362 |
| 2,126,070 | 8/1938 | Wappler | 128/172.1 |
| 2,355,231 | 8/1944 | Moore | 128/172.1 |
| 2,667,162 | 1/1954 | Zwahlen | 128/172.1 |
| 3,490,440 | 1/1970 | Mosner et al. | 128/2.1 E |
| 3,534,727 | 10/1970 | Roman | 128/2.06 E |
| 3,542,010 | 11/1970 | Love | 128/2.1 E |

FOREIGN PATENTS OR APPLICATIONS

| | | | |
|---|---|---|---|
| 399,147 | 6/1909 | France | 128/172.1 |

*Primary Examiner*—Robert W. Michell
*Assistant Examiner*—Lee S. Cohen
*Attorney, Agent, or Firm*—Theodore B. Roesssel; J. Stephen Yeo

[57] ABSTRACT

An electrode for use in low intensity direct current therapy of skin lesions and the like. The electrode contains silver from which silver ions are carried to the treatment site under the influence of direct current to provide a germicidal action at the lesion. The electrode may have a porous support structure and some of the silver may be chlorided. The electrode is maintaned in substantially direct contact with the treatment site while being saturated with an electrolyte similar to tissue fluids.

2 Claims, 2 Drawing Figures

METHOD OF USING ELECTRODES HAVING ANTISEPTIC PROPERTIES FOR LIDC THERAPY

BACKGROUND OF THE INVENTION

This invention relates generally to electrotherapy and more particularly concerns electrodes for low intensity direct current generators.

In recent years, low intensity, direct current therapy (LIDC) has become a medically accepted method for the treatment of skin ulcers, surface wounds and the like. It has been found that the proper application of LIDC yields a beneficial factor for skin trauma and accelerates the healing process of various skin lesions by stimulating tissue growth.

The open lesions and ulcers to be treated by LIDC are often infected with pathogens such as bacteria. As to be discussed later in fuller detail, your applicant has succeeded in combining the features of LIDC therapy with the known antiseptic properties of silver and silver salts by using the low intensity direct current to affect ion transfer of germicidal silver ions to the lesion or ulcer in a manner not to be confused with iontophoresis.

For LIDC therapy, direct current of the proper magnitude is directed through the lesion by means of electrodes mounted upon the skin in proximity to the lesions. An example of apparatus providing a constant level of direct current to electrodes is disclosed in a copending application by Anton Horn, Electrotherapy Device, U.S. Pat. No. 3,918,459. Electrodes containing particulate silver or carbon in a non-porous elastomer structure have been used for LIDC therapy. These electrodes are typically applied to the patient's skin by means of adhesive tape while interposed between the electrodes and the skin are several layers of gauze saturated with conductive electrolyte such as Ringer's solution to lower the interface resistance. Such electrodes perform no function other than to conduct the current from the LIDC generator to the body.

Iontophoresis apparatus is old in the electrical therapeutic art. U.S. Pat. No. 3,289,671, Iontophoresis method by E. T. Trotman et al. filed Sept. 11, 1963, describes an apparatus providing a constant current source for practicing iontophoresis. Iontophoresis is usually carried out by applying positive and negative electrodes to opposite side of a body member such as the forearm. One electrode rests on an absorbent pad which is applied to the skin and saturated with a liquid drug susceptible to ionization so that when electric current is applied to the electrodes ions of the drug molecules pass from one electrode into the skin towards the other electrode. The drug is usually dissolved in a fluid which normally is comprised of a solvent and the ionic medicament to be applied. The solvent used for iontophoresis is substantially non-conductive so that the medicament constitutes substantially the only current in the electrolyte fluid. Simple aqueous solutions have most commonly been used for the electrolyte.

Iontophoresis treatment requires currents of the magnitude of 2 milliamps whereas the current found benefical for germicidal LIDC therapy is in the order of 10 microamps.

Electrodes containing a mixture of silver and silver salts, such a silver chloride are known in the electrocardiograph art. U.S. Pat. No. 3,574,305, Detection of Electrophysicological Potentials or of Currents by Gerhard Muhl, and U.S. Pat. No. 3,834,373, Silver, Silver Chloride Electrodes by Takuya R. Sato, are two of many examples of silver silver chloride electrodes intended for the use in the field of cardiology for measurement of electrocardiograms. These electrodes are to be separated from the skin by means of conductive gel which effectively prevents silver migration to the wound, preventing the germicidal effect of silver ions.

SUMMARY OF THE INVENTION

An electrode for use in low intensity direct current therapy of skin lesions and the like. The electrode contains silver from which ions of which are carried to the treatment site under the influence of direct current to provide a germicidal action at the lesion. The electrode may have a porous support structure and some of the silver particles may be chlorided. The electrode is maintained in substantially direct contact with the treatment site while being saturated with an electrolyte.

DETAILED DESCRIPTION OF THE DRAWINGS

Figure 1:
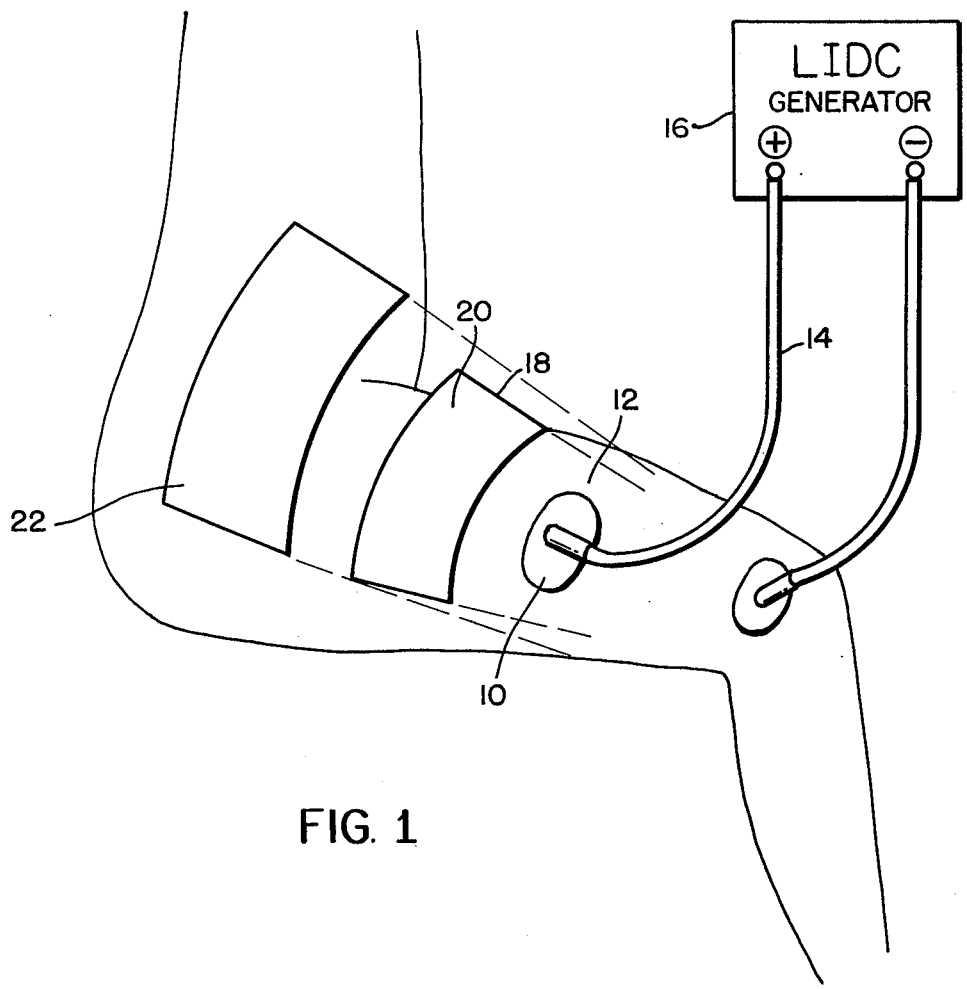
FIG. 1 illustrates a method for practicing the present invention.
Figure 2:
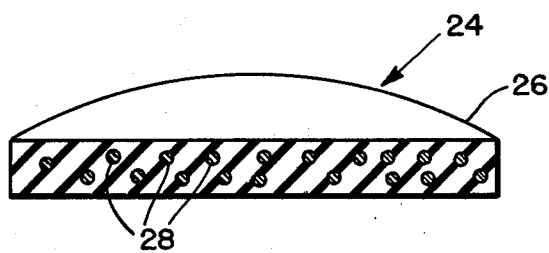
FIG. 2 is a cross-sectional view of an electrode suitable for practicing the invention.

In accordance with the invention, FIG. 1 is an exploded view of a silver bearing electrode 10 positioned over a section of tissue 12 be treated by simultaneous low intensity direct current therapy and ionic transfer germicidal therapy. The electrode may be made of silver foil or as shown in FIG. 2, to be described later. The electrode is electrically connected by wire 14 to a suitable LIDC generator 16 such as disclosed in U.S. Pat. No. 3,918,459, Electrotherapy Device, by Anton Horn. It is necessary to provide a return path the generator to complete the circuit so another electrode may be used as a cathode. LIDC generators are usually constant current sources capable of supplying current to the treatment site, the beneficial range being approximately between 1 and 800 microamps. Optimum current using silver electrodes for anti-bacterial effect is in the lower range of 0.1 microamps (100 nanoamps) to 50 microamps, preferably is less than 10 microamps. This has been determined to be lethal to bacterial cells but to have no significant effect on peripheral blood cells or on bone marrow cells.

In departure from the prior art, the positive electrode 10 is maintained in direct contact with the site to be treated 12 without gels or saturated gauze pads interposed between electrode and the patient. Covering the electrode is absorbent material 18, such as surgical gauze, saturated with conductive fluid or electrolyte 20.

The preferred electrolyte is the well known and available Ringer's solution. This solution is a liquid containing 800 mg. of sodium chloride, 30 mg. of potassium chloride and 33 mg. of calcium chloride and 100 ml. of sterile water and has the same concentration of sodium, potassium, calcium and chloride ions found in human plasma and extra cellecular fluid. Ringer's solution is often used for subcuteneous or intravenous injection as it is compatable with the tissues of the treatment.

If the electrode is porous the gauze can leak electrolyte through the electrode to the skin, or if the electrode is solid the electrolyte can leak around the electrode so as to maintain low interface resistance by keeping the electrode wet.

Gauze 18 and electrode 20 are held on to the area to be treated by means of adhesive tape 22 which also prevents evaporation of the solution 20.

Upon application of positive voltage the electrode becomes an anode and atomic silver ions are transferred between the interface of the electrode and the lesion to be treated. Approximately 5 micrograms of silver per milliliter of tissue fluid is the desired concentration of ionic silver. Distance of silver ion migration is limited, therefore the need for relatively direct contact between the electrode and the lesion.

FIG. 2 represents an electrode 24, also in accordance with the invention, suitable for practicing the above method. A matrix or mesh of fabric, such as nylon is provided as a support member 26 which have silver particles 28 (shown greatly enlarged in size) disposed throughout the weave. Such material is commercially available from such sources as Technical Wire Products Inc., Cranford, New Jersey, Dacron is also suitable. A disk 2.44 inches in diameter and 0.060 inches thick has found suitable for an average size lesion. Fabric can be cut to size of wound and can be backed with a Si C pad (not shown) for pressure and electrical contact.

In accordance with a further aspect of the invention, some of the silver may be in the form of silver chloride.

Chlorided electrodes were found to be more consistent in bactericidal effects than unchlorided electrodes and also effective over larger area of medium in vitro. Furthermore, lower values of LIDC current may be used (less than one microamp). In addition, the use of chlorided silver impregnated nylon mesh appears to be an effective method of maintaining antiseptic conditions in a wound undergoing LIDC treatment over a weekend without current.

A method for chloriding the silver particles in the electrode comprises of placing the silver containing mesh into a chloriding solution and passing positive current through it. Current at a controlled level of approximately 100 milliamp seconds per square cm. of mesh is used. The chloriding solution may be NaCl or KCl or Ringers solution.

The present invention provides a treatment for infected wounds to aid the healing thereof of LIDC while providing germicidal action with improved efficiency and consistency. Also the infected wound may be treated for periods of time when current is not conveniently available as the electrodes disclosed in the present invention will arrest further bacterial activities. Only very slight chloriding is required as compared to that normally required for an electro-chemical and electro-physiological electrode. In addition, the method of using this and similar electrodes uses much lower current levels than that used for iontophoresis treatment such as known in the prior art, thereby allowing LIDC treatment to be maintained simultaneously.

Thus, there has been provided, in accordance with the invention, an electrode which combines the therapeutic effects of low intensity direct current with the germicidal effects of ionic transfer of silver.

I claim:

1. A method of treating skin ulcers, lacerations, wounds and the like, wherein said method comprises the steps of:
    a. maintaining a first side of a silver-silver choride bearing porous electrode in substantially direct contact with the skin;
    b. providing an electrolyte solution on the second side of said electrode so that said electrolyte is carried through the porous electrode; and
    c. maintaining a positive direct current flow through said electrode so that said electrode is an anode.

2. A method as set forth in claim 1, wherein said current flow is in the approximate range of one hundred nanoamps to 50 microamps.

* * * * *